United States Patent
Buchanan et al.

(10) Patent No.: US 6,258,962 B1
(45) Date of Patent: Jul. 10, 2001

(54) PROCESS FOR PRODUCING ALKYLENE CARBONATES

(75) Inventors: J. Scott Buchanan, Trenton; Clarence D. Chang, Princeton; Robert A. Crane, Monroeville, all of NJ (US); Lorenzo C. DeCaul, Wilmington, DE (US); Zhaozhong Jiang, Thorofare, NJ (US); Jose G. Santiesteban, West Chester, PA (US); Hye Kyung Cho Timken, Woodbury, NJ (US)

(73) Assignee: Mobil Oil Corp., Fairfax, VA (US)

( * ) Notice: Subject to any disclaimer, the term of this patent is extended or adjusted under 35 U.S.C. 154(b) by 0 days.

(21) Appl. No.: 09/332,725

(22) Filed: Jun. 14, 1999

(51) Int. Cl.$^7$ .................................................. C07D 321/00
(52) U.S. Cl. ........................ 549/228; 549/229; 549/230
(58) Field of Search .................................... 549/228, 229, 549/230

(56) References Cited

U.S. PATENT DOCUMENTS

| | | | |
|---|---|---|---|
| 2,773,070 | 12/1956 | Lichtenwalter et al. | 260/340.2 |
| 3,748,345 | 7/1973 | De Pasquale et al. | 260/340.2 |
| 4,166,773 | 9/1979 | Higley et al. | 203/72 |
| 4,221,727 | 9/1980 | Tsang et al. | 260/348.37 |
| 4,226,778 | 10/1980 | Venturello et al. | 260/340.2 |
| 4,233,221 | 11/1980 | Raines et al. | 260/340.2 |
| 4,313,945 | 2/1982 | McMullen et al. | 260/340.2 |
| 4,325,874 | 4/1982 | Jacobson | 260/340.2 |
| 4,344,881 | 8/1982 | Strege et al. | 549/229 |
| 4,353,831 | 10/1982 | Strege et al. | 549/229 |
| 4,508,927 | 4/1985 | Bhise et al. | 568/858 |
| 4,519,875 | 5/1985 | Becker et al. | 203/28 |
| 4,691,041 | 9/1987 | Duranleau et al. | 558/277 |
| 4,786,741 | 11/1988 | Sachs | 549/230 |
| 4,851,555 | 7/1989 | Weinstein | 549/518 |
| 4,877,886 | 10/1989 | Ream | 549/230 |
| 4,931,571 | 6/1990 | Weinstein | 549/230 |
| 4,952,542 | 8/1990 | Ream | 502/27 |
| 5,138,073 | 8/1992 | Harvey | 549/230 |
| 5,179,214 | 1/1993 | Marquis et al. | 549/230 |
| 5,391,767 | 2/1995 | Mais et al. | 549/229 |
| 5,498,743 | 3/1996 | Shih et al. | 558/277 |
| 5,625,104 | 4/1997 | Beck et al. | 585/475 |
| 5,763,691 | 6/1998 | Kawabe et al. | 568/867 |

OTHER PUBLICATIONS

McMillan, Thomas I., "Ethylene Oxide Derivatives", *PEP Report No. 193* (*SRI International*), pp. 8–1 to 8–22, A–29 to A–35 and E–3 to E–15 (Jan. 1991).

*Primary Examiner*—Amelia Owens

(57) ABSTRACT

A process for the synthesis of alkylene carbonates, such as ethylene carbonate, by reacting alkylene oxides with carbon dioxide in the presence of a porous solid support catalyst containing an alkali or alkaline earth metal component.

10 Claims, No Drawings

PROCESS FOR PRODUCING ALKYLENE CARBONATES

BACKGROUND OF THE INVENTION

This invention relates to a process for the synthesis of alkylene carbonates. More specifically the invention relates to a process for the synthesis of alkylene carbonates by reacting alkylene oxides with carbon dioxide in the presence of a porous solid support catalyst containing an alkali or alkaline earth metal component.

Alkylene carbonates, such as ethylene carbonate and propylene carbonate, are useful as specialty solvents, hydraulic fluid additives and intermediates in numerous chemical processes. For example, ethylene carbonate is useful as an intermediate in polycarbonate manufacture, as discussed more fully below, as well as in the manufacture of ethylene glycol.

The traditional method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, such as reacting bisphenol-A with diphenyl carbonate that can be synthesized from dimethyl carbonate and phenol.

Dimethyl carbonate has a low toxicity and can be used to replace toxic intermediates, such as phosgene and dimethyl sulphate, in many reactions, such as the preparation of urethanes and isocyanates, the quaternization of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other dialkyl carbonates, have traditionally been produced by reacting alcohols with phosgene. These methods have the same problems as methods that use phosgene and bisphenol-A, i.e., the problems of handling phosgene and phosgene waste materials. Therefore, non-phosgene methods for the production of dimethyl carbonate, as well as other dialkyl carbonates have been developed. For example, U.S. Pat. No. 5,498,743 discloses a method for producing dialkyl carbonates, such as dimethyl carbonate, by reacting alkylene carbonates with alcohols. Thus, there is a significant market for commercially viable methods for the production of ethylene carbonate, as well as other alkylene carbonates, for use as intermediates in such a process.

Reaction of alkylene oxides with carbon dioxide in the presence of various catalysts to produce alkylene carbonates is known in the art. For example, homogeneous catalysts such as ammonium, phosphonium and sulphonium salts; a combination of protic compounds and nitrogen-containing bases; arsonium halides; tertiary phosphines; nitrogen bases; and alkali or alkaline earth metal halides have been proposed.

However, there are problems associated with using many of these proposed homogeneous catalysts in an industrial process. The problems include low selectivities to the desired alkylene carbonate, long reaction times (e.g. 5 hours or more) and the use of a relatively high amount of catalyst. Moreover, many of these catalysts can lose their activity during recycling and, therefore, require the disposal of a large amount of inactive spent catalyst.

Additionally, while some of these catalysts may provide adequate selectivities and reaction rates, they often are difficult to separate from the product stream or from by-products of the reaction. For example, a continuous process for the preparation of ethylene carbonate from ethylene oxide and carbon dioxide, using a potassium iodide catalyst, exhibits such a problem. Although the use of potassium iodide as a catalyst in such a process may provide an adequate selectivity and reaction rate, a significant amount of the potassium iodide is generally lost due to the difficulty of recovering the catalyst from the by-product or purge stream. Specifically, this reaction, between ethylene oxide and carbon dioxide, will produce polyglycols as by-products, which will generally be removed by way of a purge stream. Since the potassium iodide is highly soluble in these polyglycols, it is difficult to separate from them. As a result, the potassium iodide will either be removed with the polyglycols or require additional equipment and expense to separate the potassium iodide from the polyglycols.

The use of heterogeneous catalysts in the reaction of alkylene oxides with carbon dioxide has also been proposed. Examples of such heterogeneous catalysts include an anion exchange resin having a quaternary ammonium salt as an exchange group and a heteropolyacid based on an oxide of tungsten or an oxide of molybdenum and a salt thereof. Although such catalysts may avoid some of the problems associated with the homogeneous catalysts, as discussed above, they have relatively slow kinetics and can only be regenerated under limited conditions.

Thus, there is a need for an economical method of producing alkylene carbonates which does not have the above-mentioned disadvantages.

SUMMARY OF THE INVENTION

According to the present invention, it has now been found that an alkylene carbonate, and more specifically ethylene carbonate, can be prepared according to a catalytic process having a relatively high reaction rate and a catalyst system which is easily regenerated, by reacting an alkylene oxide (ethylene oxide in the case of ethylene carbonate) with carbon dioxide in the presence of a porous solid catalyst containing an ion, metal, compound or complex of an element of groups IA or IIA of the periodic table.

Preferably, the alkylene carbonate is of the formula:

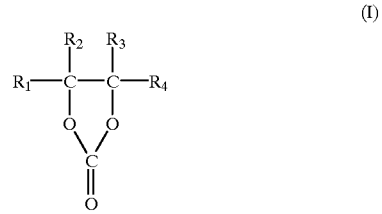

(I)

or the formula:

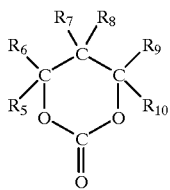

(II)

and the corresponding alkylene oxide is of the formula:

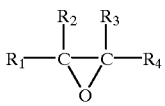

(III)

or, respectively, of the formula:

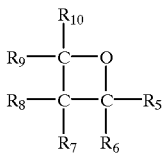

(IV)

wherein:

$R_1$, $R_2$, $R_3$ and $R_4$ independently of one another denote hydrogen; $C_1$–$C_{20}$ linear or branched, substituted or unsubstituted alkyl; $C_2$–$C_{20}$ linear or branched, substituted or unsubstituted vinyl; or $C_6$–$C_{20}$ substituted or unsubstituted aryl radicals; and any two of $R_1$, $R_2$, $R_3$ or $R_4$, together, with one or both of the two C atoms of the three-membered ring, can denote a saturated carbocyclic ring having 5–20 ring members; and, wherein:

$R_5$, $R_6$, $R_7$, $R_8$, $R_9$ and $R_{10}$ independently of one another denote hydrogen; $C_1$–$C_{20}$ linear or branched, substituted or unsubstituted alkyl; $C_2$–$C_{20}$ linear or branched, substituted or unsubstituted vinyl; or $C_6$–$C_{20}$ substituted or unsubstituted aryl radicals.

In an embodiment of the present invention, ethylene oxide is reacted with carbon dioxide in the presence of a solid catalyst having a crystalline porous support structure and an alkali or alkaline earth metal component, to produce ethylene carbonate.

In another embodiment, the invention provides for the production of ethylene carbonate by reacting ethylene oxide with carbon dioxide in the presence of a base-exchanged zeolite containing Group IA or IIA metal cations.

The present invention provides the advantage of producing alkylene carbonates, such as ethylene carbonate, with a relatively high yield and selectivity to the desired carbonate, and a catalyst system which is simple and economical to regenerate.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF PREFERRED EMBODIMENTS

Alkylene oxides that may be employed in the reaction of the present invention preferably include those of the epoxide or oxirane family and those of the oxetane family. The epoxide or oxirane compounds have a three membered ring containing a ring oxygen atom attached to two adjacent carbon atoms. The oxetane compounds have a four membered ring containing a ring oxygen atom attached to two adjacent carbon atoms, wherein each of the two carbon atoms are attached to a third ring carbon atom.

Preferably, the epoxide or oxirane compounds are represented by structural formula (III) above and the oxetane compounds are represented by structural formula (IV) above. The corresponding alkylene carbonates formed are represented by structural formulas (I) and (II), respectively.

The reaction involving the epoxide or oxirane compounds may be represented by the following:

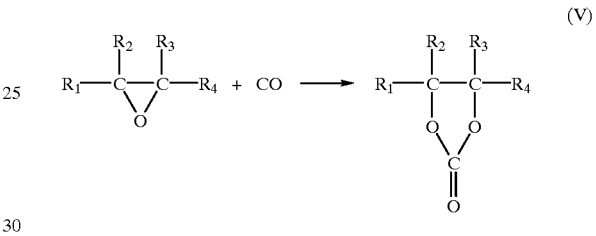

(V)

wherein $R_1$, $R_2$, $R_3$ and $R_4$ independently of one another denote hydrogen; $C_1$–$C_{20}$ linear or branched, substituted or unsubstituted alkyl; $C_2$–$C_{20}$ linear or branched, substituted or unsubstituted vinyl; or $C_6$–$C_{20}$ substituted or unsubstituted aryl radicals; and any two of $R_1$, $R_2$, $R_3$ and $R_4$, together, with one or both of the two C atoms of the three-membered ring, can denote a saturated carbocyclic ring having 5–20 ring members.

The reaction involving the oxetane compounds may be represented by the following:

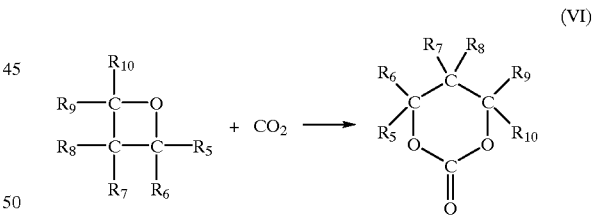

(VI)

wherein $R_5$, $R_6$, $R_7$, $R_8$, $R_9$ and $R_{10}$ independently of one another denote hydrogen; $C_1$–$C_{20}$ linear or branched, substituted or unsubstituted alkyl; $C_2$–$C_{20}$ linear or branched, substituted or unsubstituted vinyl; or $C_6$–$C_{20}$ substituted or unsubstituted aryl radicals.

The carbon dioxide to be employed can contain inert gases, such as nitrogen, hydrogen, carbon monoxide and lower hydrocarbons, and can originate from natural sources or industrial waste gases.

The content and amount of carbon dioxide will depend on the reaction rate, reactor type and specific catalyst used, and is adjusted to maximize the economics of the process. Preferably, the molar ratio of alkylene oxide to carbon dioxide is about 1:1, but an excess of carbon dioxide is also contemplated.

Therefore, according to the invention, the molar ratio of alkylene oxide to carbon dioxide is preferably in the range from about 1:0.9 to 1:15 and more preferably in the range from about 1:1 to 1:3.

The reactants (i.e., the alkylene oxide and the carbon dioxide) are contacted in the presence of a porous solid catalyst containing an absorbent substrate or support structure with a Group IA or IIA metal component. For purposes of this application, a working definition of "porous" is a material that absorbs at least 1 gram of a small molecule, such a Ar, $N_2$, n-hexane or cyclohexane, per 100 grams of the solid.

Absorbent substrates or supports which are useful in the method of this invention include porous, high surface area solids, such as activated carbon, inorganic ion-exchange materials, polymeric resins (both gel and macro-reticular types), molecular seives, zeolites, silica, alumina, magnesia, silica-alumina, silica-magnesia, aluminophosphate, silicoalumina phosphate, metalloaluminophosphate, titania, zirconia, or mixtures or combinations thereof.

Specific examples of the inorganic ion exchange materials include both the naturally occurring materials such as the mineral zeolites including mordenite, clinoptilolite, erinote, sepiolite, clays and synthetic material, which include $Al_2O_3$, $SiO_2$, $SiO_2$—$Al_2O_3$, synthetic zeolites such as zeolite A, zeolite X, zeolite Y, ZSM-5 and mordenite. Inorganic ion exchange materials useful in the present invention include materials having a wide range of structural variations and porosity. These materials include materials that can be categorized as amorphous and paracrystalline supports, crystalline molecular sieves and modified layered materials, as described in U.S. Pat. No. 5,198,203, disclosure of which is incorporated herein by reference. The materials can also include materials which are categorized as microporous or mesoporous. The term "microporous" as it referes to such materials relates to pores, or channels, with diameters of less than about 20 Angstroms. The term "mesoporous" is used to indicate materials having pores, or channels, within the range of from about 13 Angstroms to about 200 Angstroms in diameter.

Important examples of materials useful in the present invention are zeolites. Examples of suitable zeolites include, but are not limited to, aluminosilicate zeolites; typical members of this class are the zeolites having the structures of ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842): ZSM-35 (U.S. Pat. No. 4,016,245); ZMS-48 (U.S. Pat. No. 4,397,827); ZSM-57 (U.S. Pat. No. 4,046,685); ZSM-58 (U.S. Pat. No. 4,417,780); M-41S (U.S. Pat. No. 5,098,684); MCM-22 (U.S. Pat. Nos. 4,954,325 and 4,962,256); MCM-41 (U.S. Pat. No. 5,098,684); MCM-49 (U.S. Pat. No. 5,236,575); and MCM-56 (U.S. Pat. No. 5,362,697). Other isostructural forms of the zeolites containing other metals instead of aluminum such as gallium, boron or iron can also be used.

The catalyst can be shaped in the form of extrudates, cylinders, multi-lobes, pellets, granules, or be structure shaped (similar to the packing of static mixers).

The metal component of the solid catalyst can be a metal or combination of metals on the support alone or in the forms of metal oxides, metal sulfides, metal chlorides, metal bromides, metal iodides and spinels and includes metal or metals of groups IA and IIA of the Periodic Table (IUPACT Table, as shown, for example, in The Merck Index, Twelfth Ed., 1996). The preferred metal or metals include sodium, potassium, rubidum, cesium, magnesium, calcium, strontium and barium. Combinations, such as Mg-Al, Ca-Al, K-Al, Cs-Al, Mg-Ga, Ca-Ga, K-Ga and Cs-Ga are also contemplated.

The catalyst is chosen to optimize the economics of the process, depending upon the particular alkylene oxide being reacted and the reaction conditions. For example, it is contemplated that cesium-based catalysts, on an alumina ($Al_2O_3$), silica ($SiO_2$) or zeolite substrate, are particularly effective for the synthesis of ethylene carbonate.

It may also be useful to incorporate the above-described catalysts with a binder or matrix of a material resistant to the temperature and other conditions employed in the process. Useful matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the above-described catalysts, ie., combined therewith, which is active, may be useful in improving the conversion and/or selectivity of the catalyst. Inactive materials may suitably serve as diluents to control the amount of conversion and/or selectivity of the catalyst. Frequently, zeolite or other crystalline materials have been incorporated into naturally occurring clays, e.g., bentonite and kaolin. These materials, i.e., clays, oxides, etc., function, in part, as binders for the catalyst . It is desirable to provide a catalyst having good crush strength, because in practice the catalyst is often subject to rough handling, which tends to break the catalyst down into powder-like materials which cause problems in processing.

Naturally occurring clays which can be composited with the above-described catalysts include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the above-described catalysts can be composited with a porous matrix material such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The weight ratio of the catalyst, e.g., zeolite, to a binder or matrix can be a wide range and is generally in the range from about 10:90 to about 90:10. The catalyst and the binder (or matrix) can be combined by any means known to one skilled in the art such as stirring, blending, kneading, or extrusion, followed by drying, where the catalyst-binder combination can be dried in air or an inert gas at a temperature in the range of from about 100° C. to about 150° C. for about 0.5 to about 12 hours. The dried catalyst-binder combination can also be further calcined, if desired, in the presence of air or an inert gas at a temperature of from about 400° C. to 700° C., preferably about 450° C. to about 600° C., for about 1 to about 12 hours. If a binder is not used, the catalyst can also be calcined alone under similar conditions to remove any contaminants, if present.

In one of its important embodiments, the present invention provides a zeolite, a calcined zeolite, or a calcined zeolite-binder combination which is treated with a compound containing an exchangeable ammonium ion to prepare an ammonium-exchanged zeolite. Examples of suitable ammonium-containing compounds include, but are not limited to, ammonium sulfate, ammonium chloride, ammonium nitrate, ammonium bromide, ammonium fluoride, and combinations thereof. Treatment of the zeolite replaces the original cations present in the as-formed zeolite with predominantly ammonium ions. Techniques for such treatment are well known to one skilled in the art such as, for example, ion exchange of the original ions. For example, a zeolite can be contacted with a solution containing a salt of the desired replacing ion or ions.

Generally, a zeolite can be slurried in an aqueous solution of an ammonium-containing compound. Preformed zeolite-binder pellets can be subjected to the ammonium exchange by circulating the exchange solution through the pellets. The concentration of the zeolite in the aqueous solution can be in the range of from about 10 to about 800, preferably about 50 to about 500 grams per liter. The amount of the ammonium-containing compound required depends on the amount of the original ion(s) to be exchanged. Upon the preparation of the solution, the solution can be subject to a temperature in the range of from about 10° C. to about 200° C., preferably about 15° C. to about 100° C., for about 1 to about 100 hours, preferably about 1 to about 50 hours depending on desired degree of ion exchange. The treatment can be carried out under a pressure in the range of from about 1 to about 10 atmospheres (atm), preferably about 1 atm or any pressure that can maintain the required temperature. Thereafter, the treated zeolite can be washed with running water for 1 to about 60 minutes followed by drying and calcining to produce a calcined hydrogen-form zeolite. The drying and calcining processes can be carried out substantially the same as those disclosed above for the preparation of a calcined zeolite or zeolite-binder.

Generally, the ammonium-exchanged zeolite becomes hydrogen-form upon a controlled calcination or high temperature treatment such that a predominant proportion of its exchangeable cations are hydrogen ions. The above-described ion exchanges of exchangeable ions in a zeolite is well known to one skilled in the art. See, for example, U.S. Pat. No. 3,700,585, which reviewed the typical ion exchange techniques employed for introducing metal cations into zeolite structures, such as techniques described in U.S. Pat. Nos. 3,140,249; 3,140,251; and 3,140,253, disclosure of which is incorporated herein by reference. Because the ion exchange procedure is well known, a detailed description of such a procedure is omitted for the sake of brevity.

Thereafter, the zeolite, whether it has been calcined or not, can be incorporated therein, or preferably impregnated or coated thereon, with a metal compound or compounds whose metal is selected from Group IA or IIA elements. Any metal compound that can promote the incorporating or impregnating of a zeolite with the desired metal of the metal compound(s) can be employed in the present invention.

Generally, any metal-containing compound that can promote the combining of the desired metal element with a zeolite can be employed herein. Examples of suitable Group IA and IIA metal compounds include, but are not limited to, NaCl, KCl, RbCl, CsCl, NaBr, KBr, RbBr, CsBr, NaI, KI, RbI, CsI, NaOH, KOH, RbOH, CsOH, $Na_2CO_3$, $K_2CO_3$, $Rb_2CO_3$, $Cs_2CO_3$, $Na_2SO_4$, $K_2SO_4$, $Rb_2SO_4$, $Cs_2SO_4$, $MgCO_3$, $CaCO_3$, $SrCO_3$, $BaCO_3$, $Mg(NO_3)_2$, $Ca(NO_3)_2$, $Sr(NO_3)_2$, $Ba(NO_3)_2$, $MgCl_2$, $CaCl_2$, $SrCl_2$, $BaCl_2$ and combinations thereof. The presently preferred metal compounds are KCl, CsCl, Kbr, KI, $Cs_2SO_4$, $Cs_2CO_3$.

A metal-promoted or metal-impregnated zeolite can be prepared by any suitable, effective means so long as the resulting zeolite can be used in the process of the present invention. Preferably, a zeolite which can have been compounded with a binder as described above and have been shaped by any means known in the art such as, for example, pelletized, extruded, tableted, or combinations of two or more thereof, can be impregnated such as, for example, by incipient wetness method with a solution, preferably aqueous solution, containing a suitable metal compound disclosed above under a condition well known to one skilled in the art such as, for example, at about 25° C. for about 1 minute to about 10 hours under atmospheric pressure. The concentrations of the metal compound in the impregnating solution and the weight ratio of this solution to the zeolite are chosen such as to provide a finished, metal-impregnated, zeolite which contains the desired content of metal. The specific amount of the Group IA or IIA metal incorporated into the catalyst will be adjusted to maximize the economics of the process and is preferably from about 1 wt % to about 50 wt % loading, based upon the total weight of the catalyst. Preferably, the base-exchange of the Group IA or IIA metal cations is accomplished under selected conditions of reagent concentration, pH, contact time, and the like, so as to eliminate substantially the base-exchangeable acid content of the zeolite. As discussed above, because the impregnation process is well known to one skilled in the art, a detailed description is omitted herein.

By eliminating substantially the base-exchangeable acid content of the zeolite, the zeolite will become essentially "non-acidic," or will exhibit substantially no acid-catalyzed reactivity when employed as a catalyst in hydrocarbon conversion systems.

The acidity and ion-exchange capacity of an aluminosilicate zeolite is generally related to the aluminum content of the zeolite. In its hydrogen form, such a zeolite will generally exhibit acid-catalyzed reactivity. However, the electrovalence of the aluminum oxide tetrahedra, i.e. $AlO_4$, of the aluminosilicate structure, will be balanced by the inclusion of Group IA or IIA cations. Thus, as the ratio of aluminum atoms to Group IA cations, such as Cs, Na, K or Li, or Group IIA cations, such as Mg/2, Ca/2 or Sr/2, approaches unity, the acid-catalyzed reactivity diminishes.

A convenient way to measure the acid-catalyzed reactivity of the catalyst is by determining its "alpha value," which is an approximate indication of its catalytic cracking activity. The alpha test is described in U.S. Pat. No. 3,354,078 and in the Journal of Catalysis, Vol. 4, 522–529 (1965); Vol. 6, 278 (1966); Vol. 61, 395 (1980), each incorporated herein by reference to that description. The present catalyst should preferably have an alpha value below about 10.

After the incorporation or impregnation with a metal compound has been completed, the metal-impregnated zeolite can then be dried, as disclosed above and then calcined. Generally the calcination is carried out in air or in an inert gas under the pressure range disclosed above. The calcination can also be carried out at a temperature in the range of about 300° to about 1000° C. for about 1 to about 30 hours, preferably about 400° C. to about 800° C. for 1 to about 20 hours, and most preferably 450° C. to 650° C. for 2 to 15 hours.

In another embodiment, the catalyst, e.g., zeolite, which may or may not be combined with a binder, may be base-exchanged directly with an ionic Group IA or IIA metal, by any method known in the art. For example, the base-exchange can be accomplished by slurring the catalyst material in an aqueous solution of a suitable Group IA compound such as sodium hydroxide, potassium chloride, cesium chloride, cesium hydroxide and the like. Of course, other Group IA or Group IIA compounds could be employed, and are contemplated. The base exchange can be accomplished under selected conditions of reagent concentration, pH, contact time, and the like. Although it is contemplated to incorporate a specific amount of alkali or alkaline ions into the catalyst, e.g., in accordance with an effort to fine-tune the activity of the catalyst, it is preferred to incorporate an amount of the desired metal ions to eliminate substantially the base-exchangeable acidic content of the as-synthesized catalyst.

In another embodiment, the catalyst, e.g., a zeolite, can be synthesized or prepared from a reaction mixture containing sources of alkali or alkaline earth metal(s), resulting in an as-synthesized catalyst which contains such alkali or alkaline metal(s). These catalysts may be synthesized by any method known in the art, such as, for example, the method described in U.S. Pat. No. 5,382,742, disclosure of which is incorporated herein by reference. The as-synthesized catalyst may be combined with a binder or matrix as discussed above.

As-synthesized catalysts useful in the present invention preferably include a zeolite, a calcined zeolite or a calcined zeolite-binder combination wherein the as-synthesized or calcined as-synthesized zeolite is essentially non-acidic.

The reaction of the present invention can be conveniently carried out either in batch or continuous operation at from about 50° C. up to about 250° C., preferably between about 100° C. up to about 200° C., and at pressures ranging from about atmospheric pressure up to about 14000 Kpa (2000 psi). In the preferred mode of operation, the reactor temperature is optimized to insure a relatively high conversion and selectivity to the desired alkylene carbonate. Although a batch operation is contemplated, the reaction will preferably be carried out in a continuous mode utilizing various reactor configurations, such as a fixed or packed-bed reactor, in a single or multiple-reactor configuration.

A packed bed provides an effective and efficient reactor. In the packed bed, the reaction zone proceeds along the direction of flow. To minimize the pressure drop across the bed and alleviate potential plugging by debris, the reactor can be operated with the bed expanded by greater than 5%. The reactor also can be operated at conditions for an ebullient bed, a fluidizing bed, or a spouting bed. The use of filters or guard beds may also prevent plugging of the catalyst bed.

In one embodiment of the present invention the alkylene oxide is ethylene oxide and the resulting alkylene carbonate is ethylene carbonate.

The reaction of ethylene oxide to produce ethylene carbonate can be carried out in a single-reactor fixed bed system. In such a single-reactor system, a source of carbon dioxide is typically passed along with ethylene oxide over the solid catalyst containing a Group IA or IIA metal. The amount of carbon dioxide present in the reaction zone is preferably a stoichiometric amount or greater relative to the ethylene oxide, based upon formula (V). The relative concentration of carbon dioxide, which can be in the gas or liquid phase, has to be optimized to achieve high-reaction selectivity to the desired ethylene carbonate product. Preferably, the solid catalyst is bound zeolite which has been ammonium-exchanged and thereafter ion-exchanged or impregnated with Cs ions.

The products from the reaction of this invention are recovered and can be separated by distillation, azeotropic distillation, extraction or other techniques well known in the art.

In another embodiment, the reaction of ethylene oxide is carried out in a fixed bed swing reactor, containing multiple reactors. In this multiple-reactor system, the fixed-bed reactors undergo alternate reaction and regeneration environments. The cycle length depends on operating conditions, plant design, and the catalytic system to be used. This multiple-reactor system approach permits the catalyst to be regenerated in a continuous manner. The method of regeneration depends on the particular catalyst used and can include any technique well known in the art.

A fluid-bed process can also be used to perform the reaction of ethylene oxide to ethylene carbonate. The fluid-bed process permits removal and make-up of fresh catalyst, thus, keeping reactor performance constant over a long period of time.

The examples set forth below are for the purpose of illustration and to describe embodiments of the best mode of the invention at the present time. The scope of the invention is not in any way limited by the examples set forth below.

EXAMPLES

The following examples have been carried out to illustrate preferred embodiments of the invention. These examples include the preparation of a base-exchanged/metal impregnated zeolite catalyst system, the preparation of a metal impregnated alumina catalyst system and the synthesis of ethylene carbonate from ethylene oxide, utilizing each of these catalyst systems.

Example 1

A Cs/MCM-22/Alumina catalyst, Catalyst A, was prepared using H-form 65 wt % MCM-22/35 wt % alumina extrudates. A physical mixture of 65 parts by weight of MCM-22 and 35 parts by weight pseudobohemite alumina powder was mulled to form a uniform mixture. The mixture was passed through a standard augur extruder to form 1/16" cylindrical shape extrudates. The extrudates were dried on a belt filter at 250° F. (121° C.) and calcined under $N_2$ at 1000° F. (538° C.) for 3 hours. The extrudates were ammonium-exchanged twice using 5 cc/g of a 1 M aqueous solution of $NH_4NO_3$ followed by drying and air calcination at 1000° F. (538° C.) for 6 hours, resulting in an H-form MCM-22/alumina extrudate. The H-form MCM-22/alumina extrudates were impregnated with 12 wt % Cs using a 20 wt % aqueous solution of Cesium Chloride via the incipient wetness impregnation method. The Cs impregnated extrudates were dried at 250° F. (121° C.) for 6 hours and then calcined in air at 1000° F. (538° C.) for 3 hours. The physical properties of the formed catalyst are listed in Table 1.

TABLE 1

| Physical Properties of the Cs/MCM-22 Catalyst | |
| --- | --- |
|  | Cs/MCM-22/$Al_2O_3$ |
| Cs Loading, wt % | 11.6 |
| Na, ppm | 140 |
| Surface area, $M^2/g$ | 314 |
| Alpha | 0.4 |

The formed catalyst, Catalyst A, was utilized in a fixed-bed catalytic experiment as follows: 2.0 g of catalyst was dispersed with sand to a total volume of 5.0 mL and loaded into a 3/8" tubular stainless steel reactor. The reactor was purged with nitrogen and heated to 200° C. at atmospheric pressure. The reactor was cooled to 80° C. and pressurized to 350 psig with carbon dioxide, flowing at 110 cc/min. Ethylene oxide was introduced to the reactor at a flow rate of 4.54 mL/hr, and the reactor temperature was increased to 100° C.

Products were condensed at approximately 200 psig and 80° C. Online liquid analysis was performed using a gas chromatograph with an FID detector. The product was found to contain 31 wt % ethylene oxide and 66 wt % ethylene carbonate. The remaining 3 wt % consisted of ethylene glycol, diethylene glycol, trimethylene glycol, tetraethylene glycol, and a small amount of unknown.

Example 1 reveals that when a feed of ethylene oxide was delivered at a flow rate of 4.54 ml/hr to a ⅜" tubular fixed bed reactor containing an excess of $CO_2$ and a total of 2.0 grams of a porous solid catalyst containing Cs, i.e. Cs/MCM-22/$Al_2O_3$, there was a relatively high selectivity to ethylene carbonate and only a relatively small amount of glycols produced. Although not demonstrated in this example, additional benefits of using such a porous solid catalyst will be realized in an industrial process, such as the ease of regenerating the catalyst.

EXAMPLE 2

A $Cs_2CO_3$-impregnated alumina catalyst, Catalyst B, was prepared from pseudobohemite alumina powder. Pure pseudobohemite alumina powder was mulled with water to form a uniform extrudable paste, and then formed into ⅛" cylindrical shape extrudates using a standard augur extruder. The extrudates were dried on a belt filter at 250° F. (121° C.). The alumina extrudates were then impregnated with Cs using a 34 wt % aqueous solution of Cesium Carbonate via incipient wetness impregnation method to achieve about 25 wt % Cs based on total catalyst weight. The Cs impregnated extrudates were dried at 250° F. (121° C.) for 6 hours and then calcined in the air at 1000° F. (538° C.) for 3 hours. The physical properties of the formed catalyst are listed in Table 2.

TABLE 2

Physical Properties of the Cs/$Al_2O_3$ Catalyst

|  | Cs/$Al_2O_3$ |
| --- | --- |
| Cs loading, wt % | 22.2 |
| Surface Area, m²/g | 101 |
| Alpha | 0 |

The formed catalyst, Catalyst B, was used in a fixed-bed catalytic experiment as follows: 8.0 g of catalyst was dispersed with sand to a total volume of 13.0 mL and loaded into a ¾" tubular stainless steel reactor. The reactor was purged with nitrogen and heated to 200° C. at atmospheric pressure. The reactor was cooled to 80° C. and pressurized to 350 psig with carbon dioxide, flowing at a rate of 220 cc/min. Ethylene oxide was introduced to the reactor at a flowrate of 9.08 mL/hr and reactor temperature was increased to 100° C.

Products were condensed at approximately 250 psig and 80° C. Online liquid analysis was performed using a gas chromatograph with an FID detector. The hydrocarbon product was found to contain 71 wt % ethylene oxide and 23 wt % ethylene carbonate. The remaining 6 wt % consisted of ethylene glycol, diethylene glycol, triethylene glycol, tetraethylene glycol, and a small amount of unknown.

Example 2 reveals that by reacting ethylene oxide with an excess of $CO_2$ in the presence of a $Cs_2CO_3$-impregnated alumina catalyst under similar conditions to Example 1, a significant amount of ethylene carbonate will be produced.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in and are within the scope of the invention as described in the appended claims.

We claim:

1. A process for preparing an alkylene carbonate comprising reacting an alkylene oxide with carbon dioxide in the presence of a porous solid catalyst, said catalyst comprising a support and ion, metal, compound or complexe of an element of Groups IA or IIA of the periodic table.

2. The process of claim 1, wherein said alkylene carbonate is of the formula:

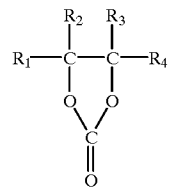

or the formula:

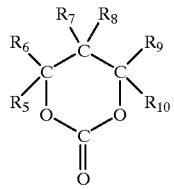

and said alkylene oxide is of the formula:

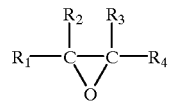

or, respectively, of the formula:

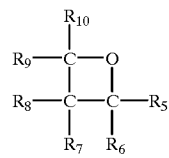

wherein:

$R_1$, $R_2$, $R_3$ and $R_4$ independently of one another denote hydrogen; $C_1$–$C_{20}$ linear or branched, substituted or unsubstituted alkyl; $C_2$–$C_{20}$ linear or branched, substituted or unsubstituted vinyl; or $C_6$–$C_{20}$ substituted or unsubstituted aryl radicals and any two of $R_1$, $R_2$, $R_3$ or $R_4$, together, with one or both of the two C atoms of the three-membered ring, can denote a saturated carbocyclic ring having 5–20 ring members; and wherein:

R$_5$, R$_6$, R$_7$, R$_8$, R$_9$ and R$_{10}$ independently of one another denote hydrogen; C$_1$–C$_{20}$ linear or branched, substituted or unsubstituted alkyl; C$_2$–C$_{20}$ linear or branched, substituted or unsubstituted vinyl; or C$_6$–C$_{20}$ substituted or unsubstituted aryl radicals.

3. The process of claim 2, wherein said alkylene carbonate further comprises ethylene carbonate and said alkylene oxide further comprises ethylene oxide.

4. The process of claim 1, wherein said support is selected from the group consisting of alumina, silica, magnesia, phosphate, zeolite, mesoporous materials, clays and mixtures thereof, in which ion, metal, compound or complexe of an element of Groups IA or IIA of the periodic table are incorporated into said support.

5. The process of claim 4, wherein said support is rendered non-acidic by base exchange prior to incorporating said ion, metal, compound or complexe of an element of Groups IA or IIA of the periodic table into said support.

6. The process of claim 4, wherein said support is synthesized in a non-acidic form.

7. The process of claim 1, wherein said porous solid catalyst further comprises a substrate which is base exchanged with Group IA or IIA metal cations to lower or essentially eliminate the base-exchangeable acidic content of the catalyst composition.

8. The process of claim 1, wherein said porous solid catalyst further comprises a base exchanged zeolite or mesoporous catalyst containing Group IA or IIA metal cations.

9. The process of claim 1, wherein the reaction is carried out in a fixed bed flow reactor.

10. The process of claim 9, wherein the reaction occurs at a temperature in the range from about 50° C. to 250° C. and at a total system pressure of from about 0 psi to 2000 psi.

* * * * *